United States Patent [19]

Cooper

[11] Patent Number: Plant 7,396

[45] Date of Patent: Dec. 18, 1990

[54] APPLE TREE TRECO SPUR RED GALA NO. 42

[75] Inventor: Calvin L. Cooper, Brewster, Wash.

[73] Assignee: Oregon Rootstock, Inc., Woodburn, Oreg.

[21] Appl. No.: 375,051

[22] Filed: Jul. 3, 1989

[51] Int. Cl.[5] ..... A01H 5/00

[52] U.S. Cl. ..... Plt./34

[58] Field of Search ..... Plt. 34

[56] References Cited

U.S. PATENT DOCUMENTS

| | | | |
|---|---|---|---|
| P.P. 3,637 | 10/1974 | McKenzie | Plt. 34 |
| P.P. 4,121 | 10/1977 | Hove | Plt. 34 |
| P.P. 5,937 | 4/1987 | De Coster | Plt. 34 |
| P.P. 6,172 | 5/1988 | Creech | Plt. 34 |
| P.P. 6,955 | 8/1989 | Kiddle | Plt. 34 |

OTHER PUBLICATIONS

Brooks, R. M., et al. (description of) "Gala", *Register of New Fruit and Nut Varieties,* (2nd Ed.) University of California Press 1972, pp. 35, 36.

T319519, Stark Bro.'s Nurseries & Orchards Co., (Trademark) Nov. 27, 1934.

*Primary Examiner*—James R. Feyrer

*Attorney, Agent, or Firm*—Eugene D. Farley

[57] ABSTRACT

A new variety of Gala apple tree discovered as a limb sport variety of Gala (Auvil cultivar) and characterized by:

1. Spur growth habit of tree.
2. Compact tree size resulting from spur growth habit.
3. Large fruit size.
4. Early and extensive red coloration while maintaining a distinctly striped color pattern.

3 Drawing Sheets

The present invention relates to a new and distinct variety of Gala apple tree known as Treco Spur Red Gala No. 42 (Cooper cultivar).

One of the most significant developments in late summer apple trees has been the development in the early 1970's of the Gala apple tree (Kidd's D-8 cultivar; U.S. Plant Pat. No. 3,637, issued Oct. 15, 1974). This new variety is a cross between the following:

| | |
|---|---|
| Red Delicious | 25% |
| Cox Orange | 25% |
| Golden Delicious | 50% |

The fruit of the Gala apple tree has had wide commercial acceptance. It is characterized by early ripening, superior flavor, and superior appearance. The tree has been propagated widely and already has been the parent of various strains, including the following:

Royal Gala, also known as the Ten Roy cultivar (U.S. Plant Pat. No. 4,121).

Scarlet Gala (U.S. Plant Pat. No. 6,172).

Galaxy Gala (U.S. Plant Pat. No. 6,955).

The Auvil cultivar (an unpatented selection from Kidd's D-8 cultivar discovered by Grady Auvil of Orondo, Wash.)

Treco Spur Red Gala No. 42 was discovered in May of 1986 by Calvin L. Cooper in the Cal Cooper cultivated fruit orchards located two miles west of Brewster, Wash., U.S.A. It was discovered growing in a block of 200 Gala apple trees, (Auvil cultivar, unpatented) as a limb sport mutation.

It was discovered on a one year growth branch having a large concentration of bloom and having also pronounced spurred and compact growth characteristics. No other comparable limb on the 200 trees comprising the block had a similar concentration of bloom.

Approximately 25 or 30 small apples set on the limb. After thinning, 9 remained.

On the rest of the 200 trees only an occasional bloom was seen. These produced only a few fruits at harvest time in August of 1986.

The spurred growth characteristics of my newly developed apple variety are shown below by relating the number of spurs formed on a given branch to the cross sectional area of the branch, in comparison with the same measurement in related Gala strains. In developing these data the vigor, pruning and root stock factors were held as constant as possible. The data were obtained from unpruned upright branches on vigorous trees having an annual growth of from 30 to 48 inches, growing either in the same blocks of trees or under cultural conditions which were maintained as closely the same as possible.

Comparative Spur Densities of Gala Strains

| Strain | P.P. No. | Shoot Cross-Sectional Srea[1] | Spur No.[2] | Spur Density[3] |
|---|---|---|---|---|
| Treco | SN 375051 | 1.25 $cm^2$ | 33 | 26.40 |
| Kidd's D-8 | 3,637 | 1.16 | 20 | 17.24 |
| Royal Gala | 4,121 | 1.09 | 23 | 21.10 |
| Scarlet Gala | 6,172 | 1.28 | 18 | 14.06 |
| "Auvil" Strain | Unpatented | 1.11 | 20 | 18.02 |

[1]Average of 10 vigorous, upright, unpruned shoots (measured 2" from point of origin).

[2]Spur counts were made at the end of the second growth season and involved the total number of spurs and shoots between origin and annual growth ring. The counts were made at the end of the 1989 season on shoots that grew in 1988, limited to growth extension occuring in 1988.

[3]Spur density was calculated by dividing shoot cross-sectional area into spur number.

Further noteworthy is the fact that the standard Gala growth habit exhibits very rapid shoot extension with growth tending to continue late into the summer. This characteristic results in a vigorous growth habit which leads to significant problems of over-crowding in plantings with high tree numbers per acre.

The Treco Gala growth habit, on the other hand, exhibits a shorter internodal distance than other Gala cultivars (1.4 cm vs. 1.7 to 1.9 cm for Kidd's D-8, Royal, and Scarlet Gala). This fact, coupled with its very high productive potential, affords a significant degree of growth control.

In addition to possessing novel growth characteristics, my new apple tree bore fruit of distinctive color and appearance.

By Aug. 20, 1986 the apples of my newly discovered variety averaged at least 90% brilliant bright red color, with stripes showing through underneath. By comparison, the fruits of the Auvil cultivar parent trees were characterized by prominent red stripes with a brilliant overlying red coloration covering about 40 to 50% of the apple.

To compare both qualitatively and quantitatively the color differences between my newly discovered Gala variety and the color characteristics of various Gala strains the following considerations are of interest:

Scarlet Gala (U.S. Plant Pat. No. 6,172) is a bright scarlet red color, uniformly over substantially the entire body of the fruit.

Galaxy Gala (U.S. Plant Pat. No. 6,955) also exhibits a solid block red appearance over the entire fruit surface.

The color of these two Gala varieties accordingly contrasts to the distinctly striped color pattern of Kidd's D-8 Gala (U.S. Plant Pat. No. 3,637), Royal or Ten Roy Gala (U.S. Plant Pat. No. 4,121) and the instant Treco Spur Red Gala No. 42 variety as illustrated in FIG. 1.

Quantitatively, comparison of the leading strains of Gala shows the following color characteristics:

Color Comparisons of the Leading Strains of Gala

| Strain | P.P. No. | Color Factor* | Color Intensity** |
|---|---|---|---|
| Treco | SN 375,051 | 95% | 3.5 |
| Kidd's D-8 | 3,637 | 27 | 1.0 |
| Royal Gala | 4,121 | 78 | 3.0 |
| Scarlet Gala | 6,172 | 81 | 4.5[1] |
| "Auvil" Strain | Unpatented | 48 | 2.2 |

*Percent of the fruit surface covered by red color typical of the Gala strain, measured with Pennwalt Color Sorter,

**Visual rating of the overall color of randomly selected fruits. Range: 1 = (color of average fruits of Kidd's D-8 strain) to 5 = (color of a solid red sphere).

[1]Color intensity of this strain tends to be very deep, at times approaching typical Red Delicious tones. Also, the color contrast where the fruits grow against a leaf, branch or other fruit is similar to "blush" strains of Delicious.

Still further, my newly discovered cultivar differed distinctly in size and shape. With respect to size, the fruits were substantially larger than were the fruits of the parent Auvil cultivar. With respect to shape, the apples of the newly discovered cultivar were more round and less conical.

Comparative fruit sizes of the various Gala apple strains are shown in the Table below, for each of two growing seasons in which crop densities were similar.

Comparative Fruit Size of Gala Strains

| Strain | Fruit Size 1987 | Fruit Size 1989 |
|---|---|---|
| Treco | 8.15 cm | 7.57 cm |
| Kidd's D-8 (Common Gala) | 7.17 | 6.92 |
| Royal Gala | 7.07 | 7.02 |
| "Auvil" Strain | 7.15 | 7.15 |

A tabulated comparison of the characteritics of the various Gala strains follows:

Consolidated Comparisons of Gala Strains

| Strain | P.P. No. | Spur Density | Fruit Size | Color Factor | L:D Ratio |
|---|---|---|---|---|---|
| Treco | SN 375051 | 26.4 | 7.89 cm | 95% | .89 |
| Kidd's D-8 | 3,637 | 17.2 | 6.25 | 27 | .94 |
| Royal Gala | 4,121 | 21.1 | 6.34 | 78 | .97 |
| Scarlet Gala | 6,172 | 14.0 | — | 81 | .96 |
| "Auvil" Strain | Unpatented | 18.0 | 6.98 | 48 | .94 |

[1]Spurs per squar centimeter of branch cross-sectional area.

[2]Consolidated three year averages of fruits on vigorous, stub-pruned, blossom thinned branches.

[3]Percent of the fruit surface covered by red color typical Gala Strain; measured with Pennwalt Color Sorter (Red × Green filters): average of four readings per fruit on several fruits of each strain.

[4]The L:D Ratio (length to diameter) is a commonly used index of fruit shape or "typeness". It indicates the more oval shape of Treco Gala.

Since discovery, Galagored No. 42 has been asexually propagated by bud grafting in the same geographic locality for three generations, during which period its unique characteristics have been shown to be stable and reproduceable.

In summary, the novel characteristics of the Cooper cultivar Treco Spur Red Gala No. 42 are as follows:

1. The spur growth habit of the tree.

The Treco Spur Red Gala No. 42 strain (Cooper cultivar) has a pronounced tendency for leaf axillary buds to develop into spurs, short shoots and branches that bloom terminally on one year old wood. This gives the tree a distinctly different growth habit from other Gala cultivars.

There is a strong tendency for the leaf axillary buds to "break" during the first season and to form short shoots and spurs. This results from a greater number of potential fruiting sites per cubic meter of tree canopy than is characteristic of other Gala cultivars. It promotes a compact tree growth habit, as opposed to the relatively loose, open growth habit of other Gala cultivars with attendant limitation on productivity. In addition, Gala fruit born on spurs tend to be larger than fruits born terminally.

2. More compact tree size resulting from spur-type growth habit.

The resulting growth control is of great significance as growers are forced, for economic reasons, to resort to greater tree densities per acre.

3. Large fruit size.

The prior art Gala cultivars typically are small — fruited apples. Measurements of 27 typical apples of the Kidd's D-8 cultivar indicate an average diameter of 2.87 inches. Examples of the Tenroy cultivar have an average diameter of 2.83 inches. Fruits of the Auvil cultivar average, in a typical example, 2.86 inches in diameter.

In contrast, the herein described Treco Spur Red Gala No. 42 apples grown in the same general area as the Auvil cultivar apples, but on somewhat greater crop densities, had an average diameter of 3.26 inches. Fruits weighing from 220 to 260 grams (approximately one-half pound) were not uncommon.

4. Early and extensive red coloration while still maintaining a distinctly "striped" color pattern.

The herein described Treco Spur Red Gala No. 42 has a very distinct red-on-red striped color pattern that covers 90 to 100% of the fruit surface. Compared to the prior art Tenroy cultivar, the intensity in the red color is greater and the extent (percent of surface covered) is also greater. Furthermore, the tone of red is somewhat deeper than that characteristic of the Tenroy cultivar.

Also, Treco Spur Red Gala No. 42 has a very smooth, bright, attractive finish with lenticels that are small and non-descript. Other cultivars of Gala have very prominent lenticels that give the fruit a "rough" finish.

The foregoing characteristics are illustrated in the accompanying drawings wherein.

Figure 1:
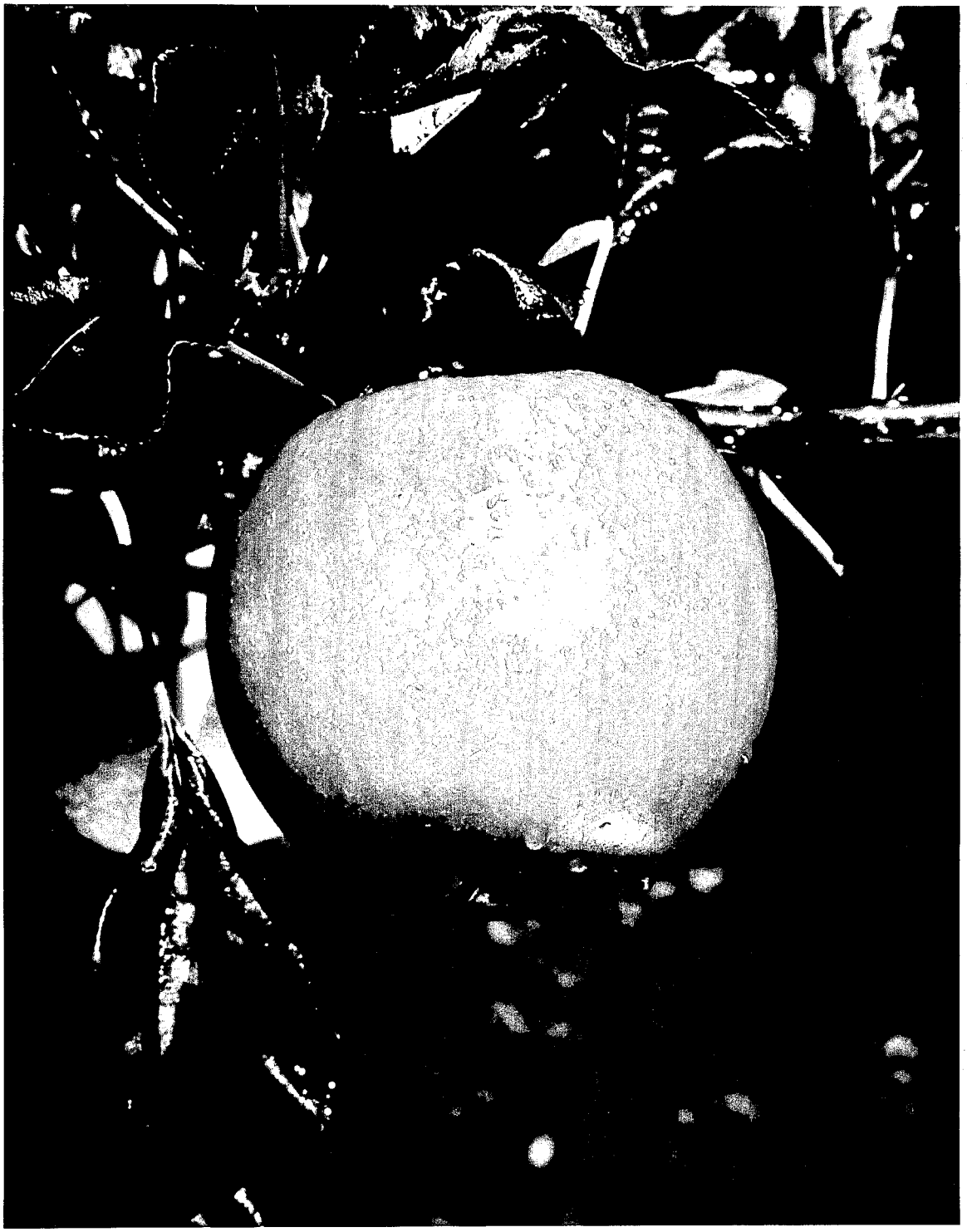
FIG. 1 is a view of the mature fruit of Treco Spur Red Gala No. 42, showing the ground color of red-on-red stripe pattern, large size, and shape characteristics of the fruit.
Figure 2:
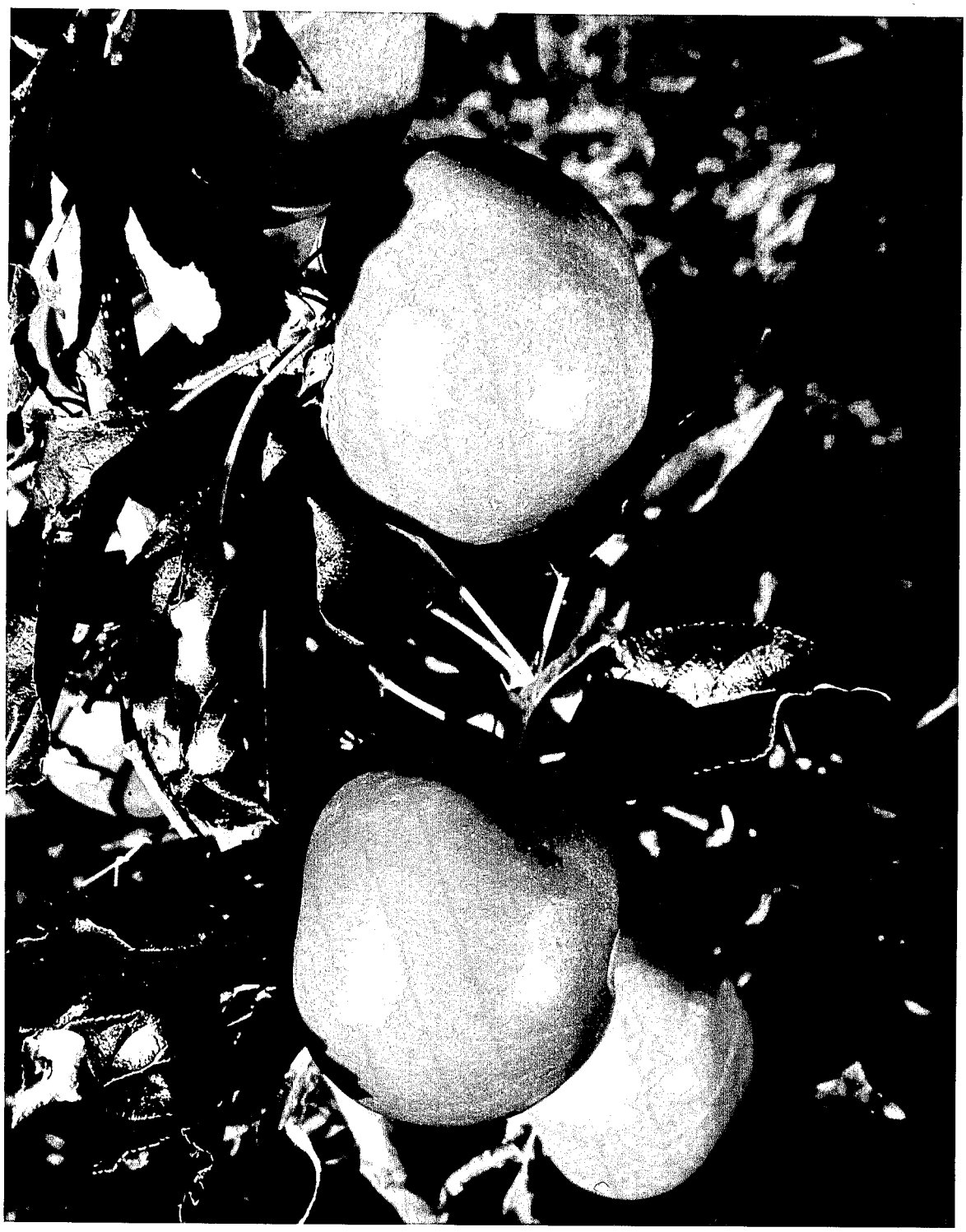
FIG. 2 is a view of a limb of Treco Spur Red Gala No. 42 apples at maturity, illustrating the spur-type growth habit of the tree and the red color patterns of the fruit.
Figure 3:
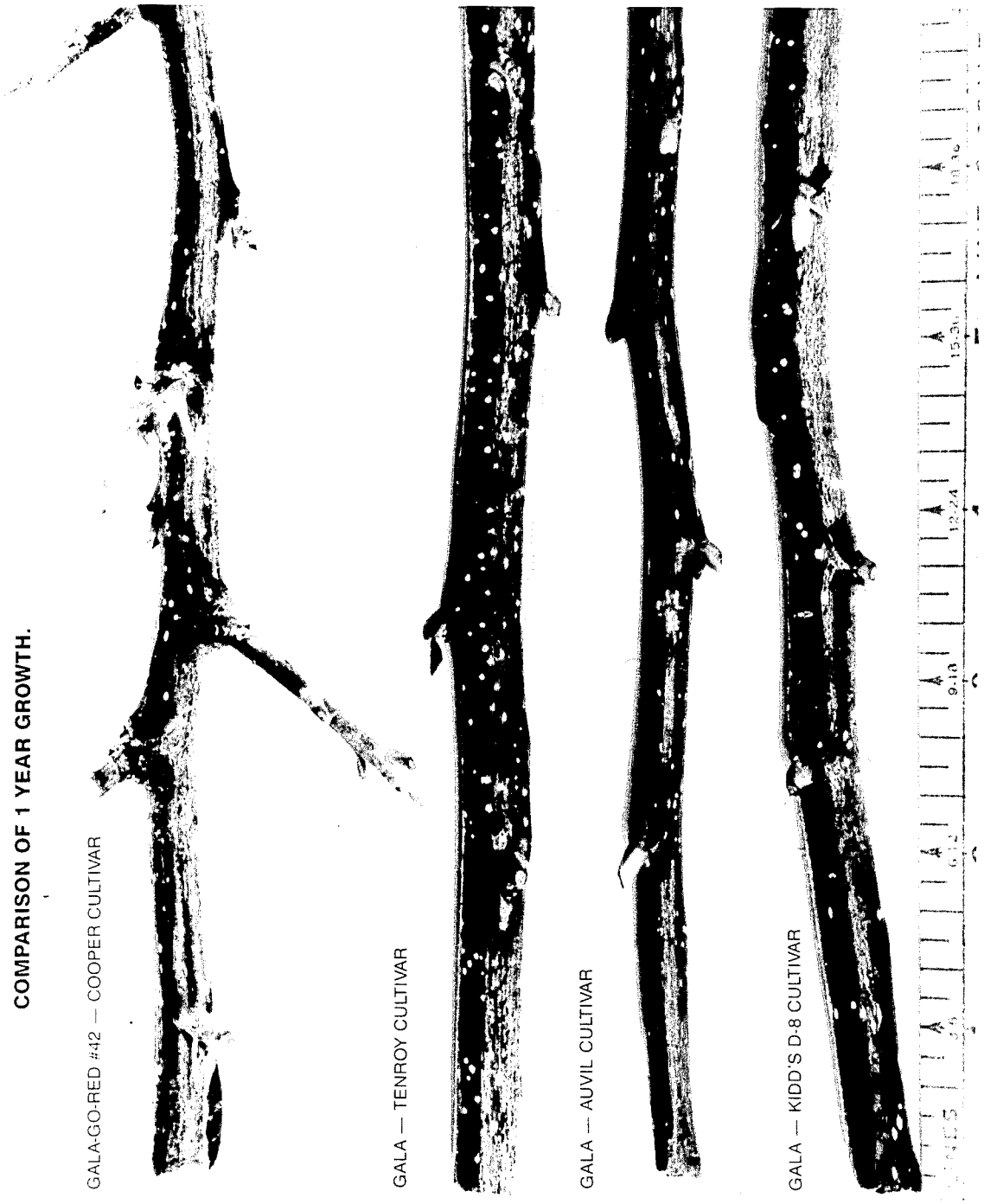
FIG. 3 is a view of the growth pattern of the limbs of Treco Spur Red Gala No. 42, as compared with the growth patterns of the Tenroy, Auvil, and Kidd's D-8 cultivars. In particular, it illustrates the desirable spur-type growth habit of Treco Spur Red Gala No. 42, as discussed hereinabove.

Considering the tree and its fruit in greater detail:

Parentage: Treco Gala was discovered as a limb sport of "Auvil Strain Gala" (unpatented selection of Kidd's D-8 strain) from tree growing at Auvil Fruit Company in Orondo, Wash., U.S.A.

Maturity date: August 22 (First Picking).

Tree: Medium size, compact, vigorous, spreading, wide branch angles, precocious, highly productive, annual bearer.

*Trunk.*—Medium thick, smooth, highly tapered.

*Branches.*—Medium thick, smooth, limber, extensively spurred.

*Leaves.*—Medium large ($3\frac{5}{8}'' \times 1\frac{7}{8}''$), thick, sharply tapered at tip, top surface-glossy, lower surface-highly pubescent, margin-finely serrate. Color: Olive green. Petiole: Long, slender, pubescent.

Flowers: Medium early (blooms with Red Delicious).

*Size.*—Medium.

*Petals.*—Single row, margin smooth, middle indentation slight.

*Color.*—White.

*Stamens.*—Single row, filaments-white, anthers-yellow turning black with pollen shed.

*Pistils.*—Stigma-prominent, stiles-fused toward base, pubescent.

*Sepals.*—Large, sharply pointed, thick.

Fruit:

*Maturity when described.*—Ripe.

*Size.*—Large, uniform.

*Shape.*—Round to oblique (L/D ratio=0.89 to 0.95.

*Cavity.*—Symmetrical, round, slightly undulate, smooth, depth $\frac{5}{8}''$, breadth 1", smooth.

*Basin.*—Symmetrical, round, slightly undulate, smooth, depth $\frac{3}{8}''$ breadth $\frac{3}{4}''$ non-pubescent.

*Stem.*—Short, medium thick.

*Calyx.*—Closed, segments lanceolate, converged toward center, pubescent.

*Skin.*—Thin, medium tough, smooth, waxy; Lenticels small more numerous toward calyx, inconspicuous: Ground color, straw-yellow (Plate XVI, Color No. 21', tone b)*. Red color, prominent (covering 85–90% of fruit surface), striped over ground color, Rose Doree (Plate I, Color No. 3, tone b)*

* Ridgeway's Color Standards Chart

*Flesh.*—Juicy, crisp, sweep, yellowish tint, fine texture, distinct aroma.

*Core.*—Symmetrical, bundles inconspicuous, lines clasping, seed cells, five in number, obtuse, smooth, open.

*Seed.*—Perfect, 2 or less per cell, length 5/16", diameter 3/16", obtuse.

Use: Market: dessert.

I claim:

1. The new and distinct variety of apple tree Treco Spur Red Gala No. 42 (Cooper cultivar) substantially as shown and described and characterized by:

spur growth habit of tree;
compact tree size resulting from spur growth habit;
large fruit size; and,
early and extensive red coloration while maintaining a distinctly striped color pattern.

* * * * *

COMPARISON OF 1 YEAR GROWTH.